(12) United States Patent
Serovy et al.

(10) Patent No.: US 9,826,941 B1
(45) Date of Patent: Nov. 28, 2017

(54) PILOT HEALTH MONITORING AND HYPOXIA PREVENTION SYSTEM AND METHOD

(71) Applicant: Rockwell Collins, Inc., Cedar Rapids, IA (US)

(72) Inventors: Rick M. Serovy, Cedar Rapids, IA (US); Charles J. Sitter, Robins, IA (US)

(73) Assignee: Rockwell Collins, Inc., Cedar Rapids, IA (US)

( * ) Notice: Subject to any disclaimer, the term of this patent is extended or adjusted under 35 U.S.C. 154(b) by 103 days.

(21) Appl. No.: 14/752,468

(22) Filed: Jun. 26, 2015

(51) Int. Cl.
*A61B 5/00* (2006.01)
*A61B 5/1455* (2006.01)

(52) U.S. Cl.
CPC .......... *A61B 5/746* (2013.01); *A61B 5/14552* (2013.01); *A61B 5/486* (2013.01); *A61B 5/6801* (2013.01); *A61B 5/7282* (2013.01); *A61B 5/742* (2013.01); *A61B 5/7405* (2013.01); *A61B 5/747* (2013.01); *A61B 5/7455* (2013.01); *A61B 2503/12* (2013.01); *A61B 2560/0475* (2013.01)

(58) Field of Classification Search
CPC ..... A61B 5/7282; A61B 5/7405; A61B 5/742; A61B 5/7455; A61B 5/747; A61B 2503/12; A61B 2560/0475; A61B 5/746; A61B 5/14552; A61B 5/486; A61B 5/6801; B64C 19/00; G01C 23/005; G05D 1/101; G08G 5/0021; G08G 5/0052
See application file for complete search history.

(56) References Cited

U.S. PATENT DOCUMENTS

| | | | | |
|---|---|---|---|---|
| 4,775,116 A | * | 10/1988 | Klein | A61B 5/14553 244/76 R |
| 5,372,134 A | * | 12/1994 | Richardson | A61B 5/02422 600/323 |
| 6,641,087 B1 | * | 11/2003 | Nelson | B64D 45/0015 244/118.5 |
| 7,792,615 B2 | * | 9/2010 | Aimar | G01C 23/00 701/11 |
| 8,138,951 B2 | * | 3/2012 | McBain | B64D 45/0015 340/5.82 |

(Continued)

OTHER PUBLICATIONS

U.S. Appl. No. 14/038,406, filed Sep. 26, 2013, Shapiro et al.

(Continued)

*Primary Examiner* — George Manuel
(74) *Attorney, Agent, or Firm* — Angel N. Gerdzhikov; Donna P. Suchy; Daniel M. Barbieri

(57) ABSTRACT

A vehicular system includes a wearable device and a computing device. The wearable device is configured to be worn by an operator of a vehicle. The wearable device includes a sensor configured to measure a physiological state of the operator. The wearable device is configured to output physiological data indicative of the physiological state of the operator or operator health alert data indicative of a determined health problem associated with the operator. The computing device includes a processor configured to receive the physiological data associated with the operator or the operator health alert data from the wearable device and to determine whether the operator is experiencing a health problem based on the physiological data or the operator health alert data.

19 Claims, 4 Drawing Sheets

(56) References Cited

U.S. PATENT DOCUMENTS

| | | | |
|---|---|---|---|
| 2004/0260470 A1* | 12/2004 | Rast | G06Q 10/06 701/300 |
| 2010/0174424 A1* | 7/2010 | Cornell | G01C 23/00 701/9 |
| 2012/0022724 A1* | 1/2012 | Botargues | G05D 1/101 701/8 |
| 2015/0102925 A1* | 4/2015 | Foldyna | A61F 7/00 340/539.12 |

OTHER PUBLICATIONS

U.S. Appl. No. 14/038,439, filed Sep. 26, 2013, Shapiro et al.
U.S. Appl. No. 14/685,455, filed Apr. 13, 2013, Wolford et al.
Withings, Pulse Ox, http://www2.withings.com/us/en/products/pulse, 7 pages, Printed online Jun. 9, 2015.

* cited by examiner

US 9,826,941 B1

PILOT HEALTH MONITORING AND HYPOXIA PREVENTION SYSTEM AND METHOD

CROSS-REFERENCE TO RELATED APPLICATIONS

The present application is related to U.S. patent application Ser. No. 14/038,406, filed on Sep. 26, 2013, to U.S. patent application Ser. No. 14/038,439, filed on Sep. 26, 2013, and to U.S. patent application Ser. No. 14/685,455, filed on Apr. 13, 2015, all of which are hereby expressly incorporated herein in their entirety.

BACKGROUND

Onboard pilots are susceptible to hypoxia or a limited oxygen supply to parts of the body when piloting aircraft. Current aircraft systems provide insufficient monitoring of onboard pilot's oxygen levels, as well as other health problems, during flight. Further, current aircraft systems fail to provide indications if a pilot's oxygen level drops to an unacceptable level.

SUMMARY

In one aspect, embodiments of the inventive concepts disclosed herein are directed to an aviation system including a wearable device and a computing device. The wearable device is configured to be worn by a pilot of an aircraft. The wearable device includes a sensor configured to measure a physiological state of the pilot. The wearable device is configured to output physiological data indicative of the physiological state of the pilot or pilot health alert data indicative of a determined health problem associated with the pilot. The computing device includes a processor configured to receive the physiological data associated with the pilot or the pilot health alert data from the wearable device and to determine whether the pilot is experiencing a health problem based on the physiological data or the pilot health alert data.

In a further aspect, embodiments of the inventive concepts disclosed herein are directed to a method. The method includes receiving, by a processor of a computing device and from a wearable device worn by a pilot, physiological data indicative of at least one physiological state of the pilot. The wearable device includes at least one sensor including an oximeter, and the physiological data includes oxygen level data. The method further includes determining, by the processor of the computing device, that the pilot is experiencing hypoxia based at least on the physiological data. The method also includes outputting, by the processor of the computing device, pilot health alert data upon a determination that the pilot is experiencing hypoxia.

In a further aspect, embodiments of the inventive concepts disclosed herein are directed to a vehicular system. The vehicular system includes a wearable device and a computing device. The wearable device is configured to be worn by an operator of a vehicle. The wearable device includes at least one sensor configured to measure at least one physiological state of the operator. The wearable device is configured to output physiological data indicative of the at least one physiological state of the operator or operator health alert data indicative of a determined health problem associated with the operator. The computing device includes a processor configured to receive the physiological data associated with the operator or the operator health alert data from the wearable device. The processor of the computing device is further configured to determine whether the operator is experiencing a health problem based on the physiological data or the operator health alert data.

Additional embodiments are described in the application including the claims. It is to be understood that both the foregoing general description and the following detailed description are exemplary and explanatory only and are not restrictive. Other embodiments will become apparent.

BRIEF DESCRIPTION OF THE DRAWINGS

Other embodiments will become apparent by reference to the accompanying figures in which.

DETAILED DESCRIPTION

Figure 1:
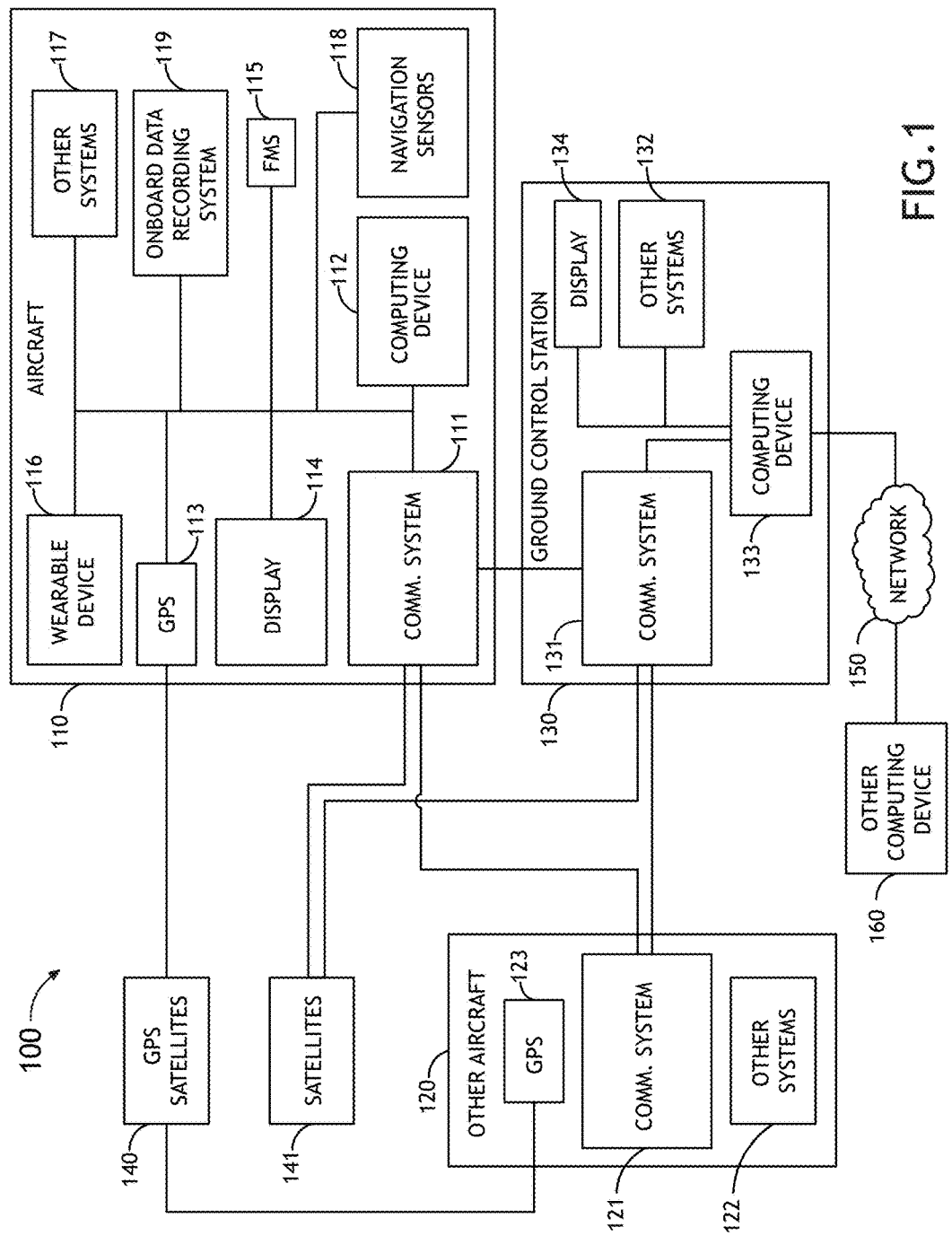
FIG. 1 shows a system topology of one embodiment.

Reference will now be made in detail to exemplary embodiments of the inventive concepts disclosed herein, which are illustrated in the accompanying drawings. The scope of the disclosure is limited only by the claims; numerous alternatives, modifications, and equivalents are encompassed. For the purpose of clarity, technical material that is known in the technical fields related to the embodiments has not been described in detail to avoid unnecessarily obscuring the description.

Embodiments of the inventive concepts disclosed herein include monitoring pilot oxygen levels while in flight so as to reduce or eliminate the occurrence of hypoxia in pilots. Some embodiments include a wearable device, which may include an oximeter that measures a person's arterial oxygen saturation ($SpO_2$) levels. In one embodiment, the wearable device may be implemented as bracelet worn on a user's wrist; however, in other embodiments the wearable device may implemented as any suitable wearable device configured to be worn on or in any suitable portion of user, such as wrist wearable device (e.g., wrist band device, or the like), a hand wearable device (e.g., a glove device, a ring device, or the like), a head wearable device (e.g., a helmet device, a goggle device, a visor device, a glasses device, a headset device, a headphone device, or the like), clothing wearable device (e.g., a sleeve device, a legging device, shirt device, or the like), an adhesively-attached device, or the like. The wearable device may be implemented as a personal activity tracker (e.g., a Fitbit, Pulse $O_2$, or the like), smart watch, or other wearable device. The wearable device may be configured to capture oxygen level data and transmit (e.g., via a connected cable or wirelessly, such as via Bluetooth or the like) the captured oxygen level data to a system implemented on a computing device onboard the aircraft. If the system determines that a user's oxygen levels are getting too low (e.g., below a predetermined threshold level), the system can issue or instruct another system to issue an alert (e.g., an aural warning or visual warning) to the user, as well as other users, that supplemental oxygen is required. Additionally, the wearable device may measure a user's other physiological states (such as heart rate, and the like) and transmit physiological data to the system. The transmitted data from the wearable device may also be recorded by an onboard data recording system. The data transmitted from the wearable device may be routed to off-board destinations (e.g., air traffic control (ATC), a ground control station, other vehicles, or the like) such as via an automatic dependent surveillance-broadcast (ADS-B) datalink or an aircraft communications addressing and reporting system (AGARS) message. Likewise, any alerts, warnings, messages, or other notifications may be communicated to other onboard systems or off-board destinations. Embodiments may detect when a pilot's oxygen levels are below a predetermined threshold and alert the pilot that the pilot is about to enter a state of hypoxia. By alerting a pilot prior to entering a state of hypoxia, the pilot would have adequate time to put on an oxygen mask to prevent hypoxia. For example, a first avionics system may send a message to a second avionics system (e.g., an engine-indicating and crew-alerting system (EICAS)) to issue a hypoxia alert (e.g., an aural hypoxia alert, a visual hypoxia alert, a vibratory hypoxia alert, a combination thereof, or the like) which indicates to a user that the user is in a state of hypoxia or near a state of hypoxia.

The wearable device may be configured to wirelessly connect and communicate with one or more avionics systems through any suitable wireless technologies and components. For example, suitable wireless technologies may include Bluetooth, Near Field Communication (NFC), a local area wireless computing network (e.g., Wi-Fi), cellular networks, a mobile telecommunications network (e.g., third generation (3G), fourth generation (4G), or the like). Similarly, suitable components may include a transmitter and/or a receiver configured to communicate via suitable wireless technologies and may include conversion devices (e.g., a wireless-to-non-wireless network conversion device, such as a Bluetooth-to-Ethernet conversion device) configured to communicatively couple different types of networks (e.g., wireless networks, non-wireless networks, or a combination thereof), a tethering device (e.g., an Aeronautical Radio, Incorporated (ARINC) 834 tethering device), a network adapter, or the like.

Referring now to FIG. 1, an overall system diagram of one embodiment is depicted. The system 100 includes an aircraft 110, a ground control station 130, other aircraft 120, global positioning system (GPS) satellites 140, satellites 141 (e.g., communication satellites), a network 150, and other computing device 160.

The aircraft 110 includes a communication system 111, at least one computing device 112 (which is also referred to as at least one aircraft computing device), a global positioning system (GPS) device 113, at least one display 114, a flight management system (FMS) 115, at least one wearable device 116, navigation sensors 118, an onboard data recording system 119, and other systems 117, equipment, and devices commonly included in aircraft. Some or all of the communication system 111, the computing device 112 (described in more detail with respect to FIG. 4), the global positioning system (GPS) device 113, the display 114, the FMS 115, the wearable device 116, the navigation sensors 118, the onboard data recording system 119, and the other systems 117 may be communicatively coupled. The aircraft 110 may accommodate one or more pilots, crew members, and/or passengers. While the system 100 exemplarily includes aircraft 110 and other aircraft 120, in some embodiments, the system 100 may include other vehicles, such as automobiles, spacecraft, trains, watercraft, or submersible craft.

The communication system 111 is configured to send and/or receive signals, data, and/or voice transmissions to and/or from other aircraft 120, the ground control station 130, satellites 141, or combinations thereof. That is, the communication system 111 is configured to exchange (e.g., bi-directionally exchange) signals, data, and/or voice communications with the other aircraft 120, the ground control station 130, the satellites 141, or combinations thereof. For example, the communication system 111 may be configured for sending and receiving FMS flight plan data, aircraft information, and autopilot commands between a device of the ground control station 130 (e.g., computing device 133) and a device of the aircraft 110 (e.g., FMS 115 or computing device 112). For example, the communication system 111 may include a transceiver and an antenna. An exemplary suitable transceiver may include a radiofrequency signal emitter and receiver; such exemplary transceiver may be configured to transmit or broadcast signals to other aircraft 120, the ground control station 130, or the like. In one embodiment, the transceiver may be implemented as a universal access transceiver (UAT) configured to send and receive automatic dependent surveillance-broadcast (ADS-B) signals. Additionally, in some embodiments, the communication system 111 includes a communication radio configured to send and receive voice communications to/from other aircraft 120, one or more control stations (e.g., ground control station 130), or combinations thereof. The communication system 111 may further include at least one processor configured to run various software applications or computer code stored in a non-transitory computer-readable medium and configured to execute various instructions or operations. Further, while the embodiment shown in FIG. 1 depicts a communication system 111 implemented on the aircraft 110, in other embodiments, a communication system 111 may be implemented on any type of vehicle, such as automobiles, spacecraft, trains, watercraft, or submersible craft. The communication system 111 may be configured to communicate via any suitable communications technology or standard.

In one embodiment, the GPS device 113 receives location data from the GPS satellites 140 and may provide the location data to any of various equipment/systems of the aircraft 110 (e.g., the communication system 111, the computing device 112, the display 114, the FMS 115, the navigation sensors 118, the onboard data recording system 119, the wearable device 116, and/or any of the other systems 117 of the aircraft 110). For example, the GPS device 113 may receive or calculate location data from a sufficient number (e.g., at least four) of GPS satellites 140 in view of the aircraft 110 such that a GPS solution may be calculated. In some embodiments, the GPS device 113 is implemented as part of the navigation sensors 118, the wearable device 116, the computing device 112, a phone (e.g., a smart phone or cell phone), another computing device (e.g. a laptop, tablet, mobile computing device, or the like), and/or the like. Further, while the embodiment shown in FIG. 1 depicts the GPS device 113 implemented on the aircraft 110, in other embodiments, a GPS device 113 may be implemented on any type of vehicle, such as automobiles, spacecraft, trains, watercraft, or submersible craft. The GPS device 113 may be configured to provide the location data to any of various equipment/systems of a vehicle. For example, the GPS device 113 may provide location data to the wearable device 116, the computing device 112, and/or another component of a vehicle such that a location may be determined of where the vehicle (e.g., aircraft 110) is when an operator (e.g., a pilot) is experiencing a health problem (e.g., hypoxia), which may be determined by monitoring a physiological state of the operator. A determined location of a where a pilot is experiencing a health problem may be provided (e.g., routed or sent) to any onboard or off-board device or system.

In one embodiment, the display 114 may include projectors (such as an image projector, a retina projector, or the like), liquid crystal cells (e.g., such that the display 114 is implemented as a liquid crystal display (LCD)), and/or light emitting diodes (LEDs) (e.g., such that the display 114 is implemented as an LED display). The display 114 may be configured to present various graphical content from any of various avionics systems. For example, the display 114 may be configured to present visual hypoxia alerts to a pilot. Additionally, the display 114 may include or be implemented as a weather display overlay, an EICAS display overlay, a head-up display (HUD), a head-down display, a head-mounted display (HMD), an integrated display system, and/or the like. In some embodiments, the display 114 includes or is implemented as a touchscreen display. In some embodiments, the aircraft 110 includes a plurality of displays 114. In some embodiments, the display 114 includes one or more components of a flight control panel. In some embodiments, the display 114 may be omitted. Further, while the embodiment shown in FIG. 1 depicts the display 114 implemented on the aircraft 110, in other embodiments, the display 114 may be implemented on any type of vehicle, such as automobiles, spacecraft, trains, watercraft, or submersible craft. The display 114 may be configured to graphically present any of various content to a user or operator of a vehicle.

The flight management system 115 may include at least one processor, memory, and storage, as well as other components, equipment, and/or devices commonly included in a flight management system. The at least one processor, the memory, and the storage, as well as other components may be communicatively coupled. The processor may be configured to run various software applications or computer code stored in a non-transitory computer-readable medium and configured to execute various instructions or operations as disclosed throughout and configured to perform any suitable functions that may be performed by an FMS. For example, the FMS 115 may be configured to send or route FMS data (e.g., data associated with a flight plan) or updated FMS data to any of various equipment/systems of a vehicle (e.g., the wearable device 116, the computing device 112, the communication system 111, other systems 117, the onboard data recording system 119, or the like). For example, the FMS 115 may provide FMS data to the wearable device 116, the computing device 112, and/or another component of a vehicle such that flight plan information (or travel plan information for other types of vehicles) of the aircraft 110 may be determined when a pilot is experiencing a health problem (e.g., hypoxia), which may be determined by monitoring a physiological state of the operator. Flight plan information of a vehicle when an operator is experiencing a health problem may be provided (e.g., routed or sent) to any onboard or off-board device or system. Additionally, for example, the FMS 115 may be configured to update or change a flight plan based on received health alert data and/or physiological data. Further, the FMS 115 may be configured to update or change a flight plan based on instructions received from at least one onboard source and/or off-board source. Additionally, the FMS 115 may be configured to send or route FMS data or updated FMS data to at least one onboard destination and/or off-board destination.

The wearable device 116 may be configured to be worn by a pilot, a crew member, or a passenger. The wearable device 116 may include a sensor (e.g., an oximeter) configured to measure arterial oxygen saturation ($SpO_2$) levels. The wearable device may be configured to transmit oxygen level data to a computing device (e.g., computing device 112) of the aircraft 110. The wearable device 116 may include any of various suitable components and may be configured to perform any of various suitable functions. In some embodiments, any number of wearable devices 116 may be worn by any number of pilots, crew members, or passengers. The wearable device 116 is described in more detail with respect to FIGS. 2A-B, below. Further, while the embodiment shown in FIG. 1 depicts wearable device 116 implemented in the aircraft 110, in other embodiments, the wearable device 116 may be implemented in any type of vehicle, such as automobiles, spacecraft, trains, watercraft, or submersible craft. The wearable device 116 may be configured to be worn by a user or operator of a vehicle.

In one embodiment, the navigation sensors 118 include sensors configured to sense any of various flight conditions or aircraft conditions typically used by aircraft. For example, various flight conditions or aircraft conditions may include altitude, position, speed, pitch, roll, yaw, air temperature, pressure, and/or the like. For example, the navigation sensors 118 may include a radio altimeter, the GPS device 113, airspeed sensors, flight dynamics sensors (e.g., configured to sense pitch, roll, and/or yaw), air temperature sensors, air pressure sensors, or the like. Additionally, one or more of the navigation sensors 118 may be included in or communicatively coupled to the wearable device 116. The navigation sensors 118 may be configured to sense various flight conditions or aircraft conditions and output data (e.g., flight condition data or aircraft condition data) to another device or system (e.g., computing device 112, the FMS 115, the wearable device 116, or the communication system 111) of the aircraft 110 or of the overall system 100. Further, while the embodiment shown in FIG. 1 depicts navigation sensors 118 implemented in the aircraft 110, in other embodiments, the navigation sensors 118 may be implemented in any type of vehicle, such as automobiles, spacecraft, trains, watercraft, or submersible craft. The navigation sensors 118 may be configured to sense any of various travel conditions or vehicle conditions. For example, the navigation sensors 118 may be configured to provide navigation data (e.g., data associated with vehicle speed, location, trajectory, altitude, vehicle dynamics (e.g., flight dynamics)) to any of various equipment/systems of a vehicle (e.g., the wearable device 116, the computing device 112, the FMS 115, the communication system 111, other systems 117, the onboard data recording system 119, or the like). For example, the navigation sensors 118 may provide navigation data to the wearable device 116, the computing device 112, and/or another component of a vehicle such that navigation information of the vehicle may be determined when an operator (e.g., a pilot) is experiencing a health problem (e.g., hypoxia), which may be determined by monitoring a physiological state of the operator. Determined navigation information of a vehicle when an operator is experiencing a health problem may be provided (e.g., routed or sent) to any onboard or off-board device or system.

The other systems 117 of the aircraft 110 may include a weather radar system, an auto-flight system, an autopilot system, an EICAS, a traffic collision avoidance system (TCAS), an aircraft communications addressing and reporting system (AGARS), and/or the like. Some or all of the other systems 117 may be communicatively coupled with one another, as well as with some or all of the components of the aircraft 110. Additionally, one or more of the other systems 117 may be included in or communicatively coupled to the wearable device 116. In some embodiments, each of the other systems 117 includes or is implemented on a separate computing device, which may include components described with respect to computing device 112. In other embodiments, some or all of the other systems 117 may be implemented on the computing device 112. In still other embodiments, the other systems 117 may be implemented on any number (e.g., at least one) of computing devices, each of which may include components described with respect to computing device 112. For example, the other systems 117 may include at least one processor configured to run various software applications or computer code stored in a non-transitory computer-readable medium and configured to execute various instructions or operations. Further, while the embodiment shown in FIG. 1 depicts other systems 117 implemented in the aircraft 110, in other embodiments, other suitable systems may be implemented in any type of vehicle, such as automobiles, spacecraft, trains, watercraft, or submersible craft. For example, the other systems 117 may be configured to provide system data (e.g., weather radar system data, auto-flight system data, autopilot system data, EICAS data, TCAS data, AGARS data, and/or the like) to any of various equipment/systems of a vehicle (e.g., the wearable device 116, the computing device 112, the FMS 115, the communication system 111, the onboard data recording system 119, or the like). For example, the other systems 117 may provide any suitable system data to the wearable device 116, the computing device 112, and/or another component of a vehicle such that such system information of the vehicle may be determined when an operator (e.g., a pilot) is experiencing a health problem (e.g., hypoxia), which may be determined by monitoring a physiological state of the operator. Determined system information of a vehicle when an operator is experiencing a health problem may be provided (e.g., routed or sent) to any onboard or off-board device or system. Further, the other systems 117 may be configured to change or update system data based on an instruction(s) from an onboard source and/or an off-board source. Additionally, the other systems 117 may be configured to change or update system data based on physiological data or health alert data received from the wearable device 116 or another onboard source.

The onboard data recording system 119 of the aircraft 110 may be configured to preserve recent history of a flight by storing (e.g., recording) various flight parameters (such as flight sensor data, control instructions, pilot data (e.g., physiological data, such as oxygen level data, heart rate data, pilot health alert data (i.e., data associated with a health alert), and/or the like) or the like) in a non-transitory storage medium (e.g., tape, hard disk drive, solid state drive, flash storage, or the like). The onboard data recording system 119 may include a flight data recorder (FDR) and cockpit voice recorder (CVR) or be implemented as separate devices (e.g., FDR and CVR). The onboard data recording system 119 may include a locator beacon. In one embodiment, the onboard data recording system 119 may include or be implemented as a computing device, which may include components described with respect to computing device 112. Further, while the embodiment shown in FIG. 1 depicts the onboard data recording system 119 implemented on the aircraft 110, in other embodiments, an onboard data recording system 119 may be implemented on any type of vehicle, such as automobiles, spacecraft, trains, watercraft, or submersible craft. In such embodiments, the onboard data recording system 119 may be configured to preserve recent history of a vehicle's travels by storing (e.g., recording) various travel parameters (such as vehicle sensor data, control instructions, operator data (e.g., physiological data, such as oxygen level data, heart rate data, and/or the like) or the like) in a non-transitory storage medium (e.g., tape, hard disk drive, solid state drive, flash storage, or the like).

In some embodiments, the computing device 112 may include or be implemented as the wearable device 116. Further, the computing device 112 may be implemented as a single computing device that includes or is configured to perform the functionality of the communication system 111, the GPS device 113, the display 114, the FMS 115, the wearable device 116, the other systems 117, the navigation sensors 118, the onboard data recording system 119, and/or the like. In some embodiments, the at least one computing device 112 may be implemented as a plurality of computing devices that collectively include and/or are collectively configured to perform the functionality of the communication system 111, the GPS device 113, the display 114, the FMS 115, the wearable device 116, the other systems 117, the navigation sensors 118, the onboard data recording system 119, and/or the like. That is, the computing device 112, communication system 111, the GPS device 113, the display 114, the FMS 115, the wearable device 116, the other systems 117, the navigation sensors 118, the onboard data recording system 119, and/or the like may be implemented on any number (e.g., at least one) of computing devices, each of which may include components described with respect to computing device 112.

In one embodiment, the other aircraft 120 includes a communication system 121, a GPS device 123, as well as other systems 122, equipment, and devices commonly included in aircraft, as similarly described with reference to the aircraft 110 above. The other aircraft 120 may be implemented as a piloted vehicle or as a remotely accessed vehicle (RAV), such as an unmanned aerial system (UAS).

In one embodiment, the ground control station 130 includes a communication system 131, at least one computing device 133 (which may also be referred to as at least one control station computing device), and at least one display 134, as well as other systems 132, equipment, and devices commonly included in a ground control station 130. Some or all of the communication system 131, the computing device 133, the display 134, and the other systems 132 may be communicatively coupled. The ground control station 130 may be implemented as a fixed location ground control station (e.g., a ground control station of an air traffic control tower) or a mobile ground control station (e.g., a ground control station implemented on a non-airborne vehicle (e.g., an automobile or a ship) or a trailer). The ground control station 130 may also be implemented as an operations center.

The communication system 131 may be configured to receive signals from and transmit signals to vehicles, such as aircraft (e.g., the aircraft 110, the other aircraft 120), and the satellites 141. That is, for example, the communication system 131 may be configured to exchange (e.g., bi-directionally exchange) signals, data, and/or voice communications with the other aircraft 120, the aircraft 110, the satellites 141, or combinations thereof. For example, the communication system 131 may be configured for sending and receiving FMS flight plan data, aircraft information, pilot data (e.g., pilot health alert data, physiological data, such as oxygen level data or heart rate data), and autopilot commands between a device of the ground control station 130 (e.g., computing device 133) and a device of the aircraft 110 (e.g., FMS 115 or computing device 112). Additionally, for example, the communication system 131 may include a transceiver and an antenna. An exemplary suitable transceiver may include a radiofrequency signal emitter and receiver; such exemplary transceiver may be configured to transmit or broadcast signals to aircraft (e.g., the aircraft 110 and/or the other aircraft 120). In one embodiment, the transceiver may be implemented as a universal access transceiver (UAT) configured to send and receive automatic dependent surveillance-broadcast (ADS-B) signals. Additionally, in some embodiments, the communication system 131 includes a communication radio configured to send and receive voice communications to/from the aircraft 110 and the other aircraft 120. The communication system 131 may further include at least one processor configured to run various software applications or computer code stored in a non-transitory computer-readable medium and configured to execute various instructions or operations. Further, while the embodiment shown in FIG. 1 depicts the communication system 131 configured to communicate with aircraft 110 and other aircraft 120, in other embodiments, the communication system 131 may be configured to communicate with any type of vehicle, such as automobiles, spacecraft, trains, watercraft, or submersible craft.

In one embodiment, the computing device 133 may be communicatively coupled to an input device (e.g., mouse, keyboard, microphone, or the like), an output device (e.g., display 134, speaker, or the like), or an input/output device (e.g., a touchscreen display, or the like) configured to interface with a user. The computing device 133 may include at least one processor (which may be referred to as at least one control station processor) configured to run various software applications or computer code stored in a non-transitory computer-readable medium and configured to execute various instructions or operations. For example, the computing device 133 may be configured to output data to an output device for presentation to a user, and the computing device 133 may be further coupled to an input device configured to receive input data from a user. In one embodiment, some or all of a plurality of computing devices (e.g., 133) are communicatively coupled to each other. In further embodiments, one or more of the at least one computing device 133 is communicatively connected to at least one other computing device 160 via one or more networks 150 (e.g., internet, intranet, or the like). For example, the other computing device 160 may comprise a computing device at a different ground control station. The computing device 133 is described in more detail with respect to FIG. 3, below.

The display 134 may include projectors (such as an image projector, a retina projector, or the like), liquid crystal cells, and/or light emitting diodes (LEDs). The display 134 may be configured to present various graphical content related to various data (such as FMS flight plan data, aircraft information, pilot data (e.g., pilot health alert data, physiological data, such as oxygen level data or heart rate data), and autopilot commands) to a user. In some embodiments, the display 134 includes or is implemented as a touchscreen display configured to operate as an input/output device. Some embodiments include a plurality of displays 134 configured to present various graphical content to one or more users.

While the embodiment depicted in FIG. 1 includes elements as shown, in some embodiments, one or more of the elements of the system 100 may be omitted, or the system 100 may include other elements. For example, one or more of the other aircraft 120, the global positioning system (GPS) satellites 140, satellites 141, the network 150, or the other computing device 160 may be optional. Additionally, while an embodiment has been depicted as including one control station (e.g., ground control station 130), other embodiments may include any number (e.g., at least one) of control stations of various types positioned or moving anywhere in a system. Further, while the embodiment shown in FIG. 1 depicts a system 100 including aircraft (e.g., 110, 120), in other embodiments, a system may include any type of vehicles, such as aircraft, automobiles, spacecraft, trains, watercraft, submersible craft, or some combination thereof. In such embodiments, a vehicle may include vehicular systems (e.g., similar to one or more of communication system 111, computing device 112, navigation sensors, 118, FMS 115, display 114, GPS 113, onboard data recording system 119, and other systems 117) and a wearable device (e.g., similar to wearable device 116) configured to be worn by a user of a vehicle.

Figure 2B:
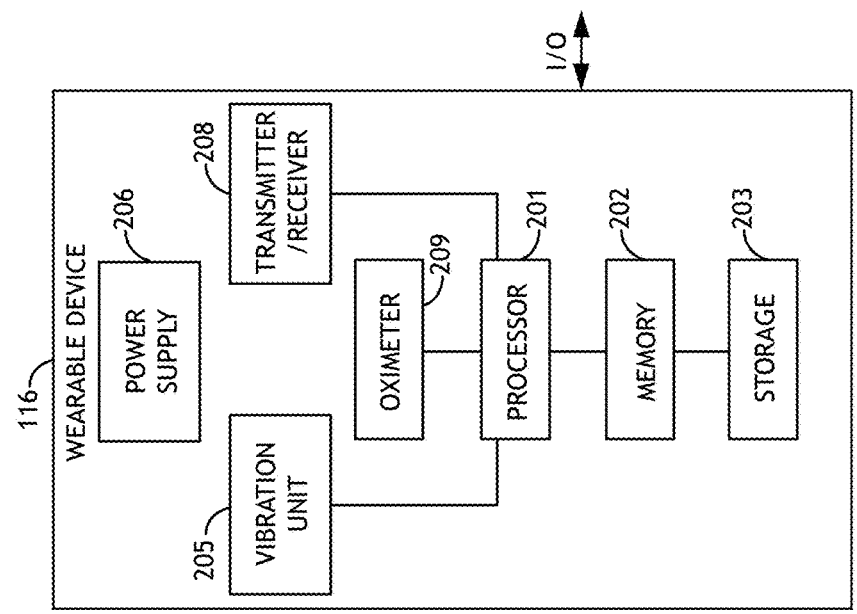
FIG. 2B depicts a diagram of a wearable device of another embodiment.
Figure 2A:
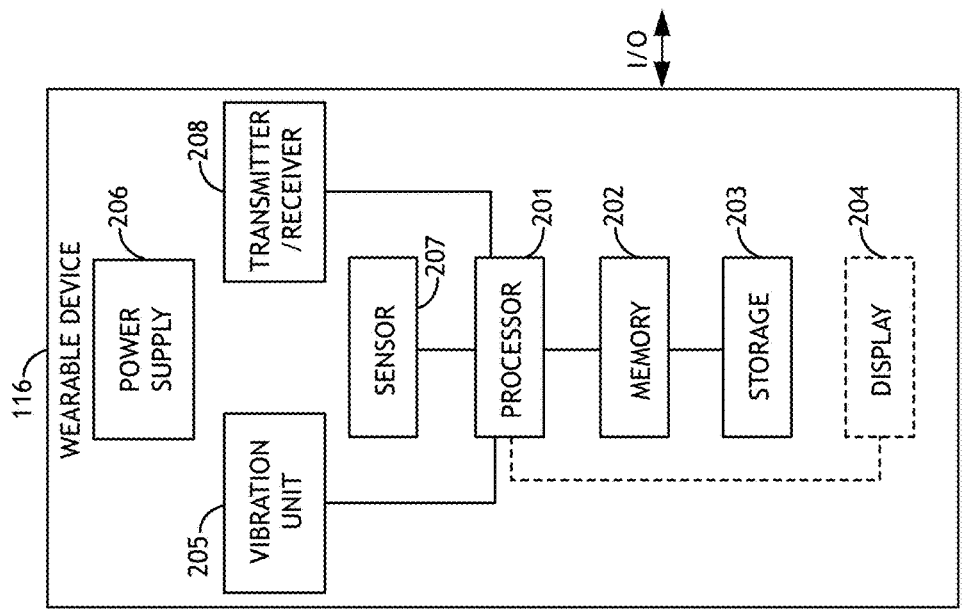
FIG. 2A depicts a diagram of a wearable device of one embodiment.

Referring now to FIG. 2A, a diagram of a wearable device 116 of one embodiment is depicted. As shown in FIG. 2A, the wearable device 116 may include a processor 201, memory 202, storage 203, one or more user output components (such as a display 204, a vibration unit 205, or the like), a power supply 206, at least one sensor 207, and a wireless communication component (e.g., transmitter/receiver 208), a user input component (such as a button or touchscreen display, which may be implemented as the display 204), as well as other components, equipment, and/or devices commonly included in a wearable computing device. The processor 201, memory 202, storage 203, display 204, vibration unit 205, and sensor 207 may be communicatively coupled. The processor 201, memory 202, storage 203, display 204, vibration unit 205, and sensor 207 may be electrically coupled to and configured to be powered by the power supply 206. The wearable device 116 may be implemented as any suitable wearable device 116, such as a wrist wearable device (e.g., a bracelet device, wrist band device, or the like), head wearable device (e.g., a helmet device, a goggle device, a visor device, a glasses device, a headset device, or the like), clothing wearable device (e.g., a sleeve device, a legging device, shirt device, or the like), an adhesively-attached device, or the like. In some embodiments, the wearable device 116 may be implemented as an in-body wearable device, for example, that may be swallowed by a user or implanted in a user's body. While the wearable device 116 of one embodiment depicted in FIG. 2A includes elements as shown, in some embodiments, one or more of the elements of the wearable device 116 may be omitted, or the wearable device 116 may include other elements.

The sensor 207 may be configured to detect or measure any of various physiological states, such as arterial oxygen saturation ($SpO_2$) levels, heart rate, or the like. For example, the at least one sensor 207 may include or be implemented as an oximeter configured to detect or measure oxygen levels (e.g. $SpO_2$ levels). The sensor 207 may provide physiological data to the processor 201. While one sensor 207 is shown in FIG. 2A, the wearable device 116 may include any number (e.g., at least one) of sensors each configured to detect or measure any of various physiological states of a user.

The processor 201 may be configured to execute various software applications, instructions, or computer code stored in a non-transitory computer-readable medium (e.g., the memory 202 or the storage 203) causing the processor 201 to perform various operations, such as disclosed throughout. For example, the processor 201 may be configured to receive physiological data from the sensor 207, user inputs, data from an onboard or off-board source, or the like. For example, the processor 201 may be configured to send (e.g., continuously, periodically at predetermined intervals, periodically upon an occurrence of a detected event or data condition, or the like) physiological data (e.g., data from the sensor 207) to an onboard destination (e.g., computing device 112, onboard data recording system 119 to be recorded, other systems 117, display 114, a wearable device associated with another user, and/or the like) and/or an off-board destination (e.g., another vehicle (e.g., other aircraft 120), ground control station 130, and/or the like). Additionally, the processor 201 may be configured for performing any of various operations on data received from the sensor 207. Further, for example, the processor 201 may be configured for performing any of various operations based on data received from the sensor 207, user input data, and/or data from an onboard or off-board source. For example, the processor 201 may be configured to monitor physiological data (e.g., oxygen level data, heart rate data, or the like) from the sensor 207. The processor 201 may determine if the pilot is experiencing any health problems (e.g., hypoxia, abnormal (e.g., low or high) heart rate, or the like) based on the physiological data. In response to a determination that the pilot is experiencing a health problem, the processor 201 may perform any of various operations. For example, in response to a determination that the pilot is experiencing a health problem the processor 201 may send data (e.g., pilot health alert data as data, an instruction, or message) to an onboard destination or an off-board destination configured to cause an alert (e.g., an aural alert such as via a speaker, a visual alert such as via a display or a light emitting diode (LED), a vibratory alert such as via a vibration unit, or the like) to be issued. Such an alert may notify the pilot to take a corrective action (e.g., to wear an oxygen mask if the pilot is experiencing hypoxia). Additionally, in response to a determination that the pilot is experiencing a health problem, the processor 201 may send data (e.g., pilot health alert data) to an onboard destination and/or an off-board destination. Further, the processor 201 may be configured to send data (e.g., as an instruction or message) to engage an auto-pilot system in response to detecting a health problem (e.g., hypoxia). Additionally, the processor 201 may be configured to alert another crew member in response to detecting a health problem (e.g., hypoxia) of a pilot.

Additionally, the processor 201 may output data as content (e.g., graphical content associated with physiological data and/or a visual alert) to be presented on the display 204 to a user (e.g., a pilot or other operator) wearing the wearable device 116.

Further, the processor 201 may be configured to activate the vibration unit 205 as a vibratory alert to a user wearing the wearable device 116.

The power supply 206 may be configured to power electronic components of the wearable device 116. For example, the power supply 206 may be implemented as a battery (e.g., a rechargeable or replaceable battery).

The wireless communication component (e.g., transmitter/receiver 208) may include or be implemented as a transmitter, receiver, and/or an antenna. The wireless communication component may be configured to wirelessly communicate (e.g., send and/or receive data or signals) with various devices of a vehicle (e.g., the aircraft 110) and/or elements of a system (e.g., system 100). For example, the wireless communication component may be configured to pair with and communicate with a computing device 112. The wireless communication component may be configured to communicate via any suitable wireless technology or standard, such as via Bluetooth, Near Field Communication (NFC), a local area wireless computing network (e.g., Wi-Fi), cellular networks, a mobile telecommunications network (e.g., third generation (3G), fourth generation (4G), or the like). Additionally, wireless communication component may include a conversion device (e.g., a wireless-to-non-wireless network conversion device, such as a Bluetooth-to-Ethernet conversion device) configured to communicatively couple different types of networks (e.g., wireless networks, non-wireless networks, or a combination thereof), a tethering device (e.g., an Aeronautical Radio, Incorporated (ARINC) 834 tethering device), a network adapter, or the like.

Referring now to FIG. 2B, a diagram of a wearable device 116 of another embodiment is shown. The wearable device 116 may be implemented and may function similarly to the wearable device 116 shown in FIG. 2A, except that the sensor of the wearable device 116 of FIG. 2B may be implemented as an oximeter 209 and that the wearable device 116 of FIG. 2B may omit a display.

Figure 3:
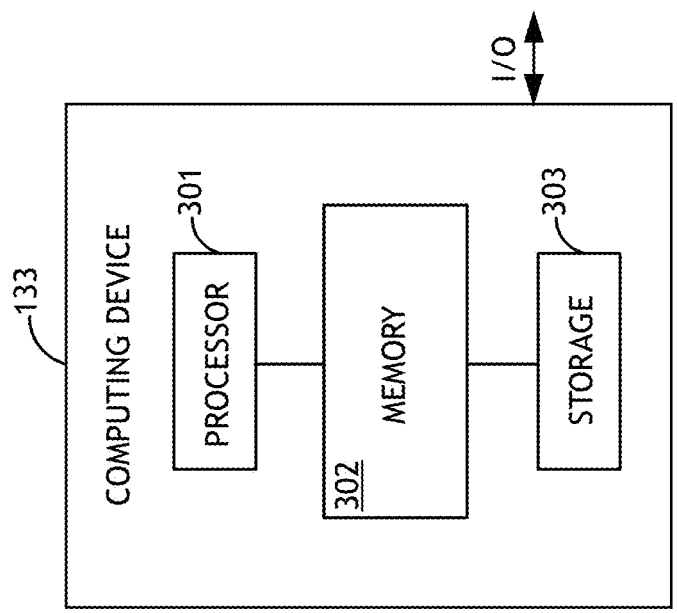
FIG. 3 depicts a computing device of a control station of one embodiment.

Referring now to FIG. 3, the computing device 133 of the ground control station 130 of one embodiment is shown. The computing device 133 includes at least one processor 301 (which may be referred to as at least one control station processor), memory 302, and storage 303, as well as other components, equipment, and/or devices commonly included in a computing device. The processor 301, the memory 302, and the storage 303, as well as any other components may be communicatively coupled. The processor 301 may be configured to execute various software applications, instructions, or computer code stored in a non-transitory computer-readable medium (e.g., the memory 302 or the storage 303) causing the processor 301 to perform various operations, such as disclosed throughout. For example, the processor 301 may be configured to receive data from any of various sources (e.g., any device, system, component, vehicle, and/or element of system 100). The processor 301 may be configured to perform any of various operations on or based on the received data, and the processor 301 may be configured to output processed data or instructions and route the processed data or instructions to any of various destinations (e.g., any device, system, component, vehicle, and/or element of system 100). For example, the processor 301 may receive physiological data and/or pilot health alert data associated with the sensor 207. The processor 301 may perform operations on the physiological data or pilot health alert data (as well as other data). The processor 301 may perform operations based on the physiological data or pilot health alert data (as well as other data) and output data. Additionally, for example, the processor 301 may be configured to monitor physiological data (e.g., oxygen level data, heart rate data, or the like) from the sensor 207. The processor 301 may determine if the pilot is experiencing any health problems (e.g., hypoxia, abnormal (e.g., low or high) heart rate, or the like) based on the physiological data. In response to a determination that the pilot is experiencing a health problem, the processor 301 may perform any of various operations. For example, in response to a determination that the pilot is experiencing a health problem the processor 301 may route data (e.g., as an instruction or message) to the aircraft 110 to cause an alert (e.g., an aural alert such as via a speaker, a visual alert such as via a display or a light emitting diode (LED), a vibratory alert such as via a vibration unit, or the like) to be issued. Such an alert may notify the pilot to take a corrective action (e.g., to wear an oxygen mask if the pilot is experiencing hypoxia). Additionally, in response to a determination that the pilot is experiencing a health problem, the processor 301 may route data to another destination (e.g., other aircraft 120, another ground control station, or the like). Further, the processor 301 may be configured to route data (e.g., as an instruction or message) to the aircraft 110 configured to engage an auto-pilot system in response to detecting a health problem (e.g., hypoxia). Also, the processor 301 may be configured to change and update a flight plan of the aircraft 110 and route an updated flight plan or FMS flight plan data to the aircraft 110 in response to a determination that the pilot is experiencing a health problem; additionally, the processor 301 may be configured to change and update a flight plan of the other aircraft 120 and route an updated flight plan or FMS flight plan data to the other aircraft 120 in response to the change and update of the flight plan of the aircraft 110. Further, the processor 301 may be configured to take control of and remotely operate the aircraft 110 in response to a determination that the pilot is experiencing a health problem, receipt of physiological data, and/or receipt of pilot health alert data. Additionally, the processor 301 may be configured to route an alert to other crew members of the aircraft 110 in response to detecting a health problem (e.g., hypoxia) of a pilot. Further, the processor 301 may be configured to receive alerts from the aircraft 110.

Figure 4:
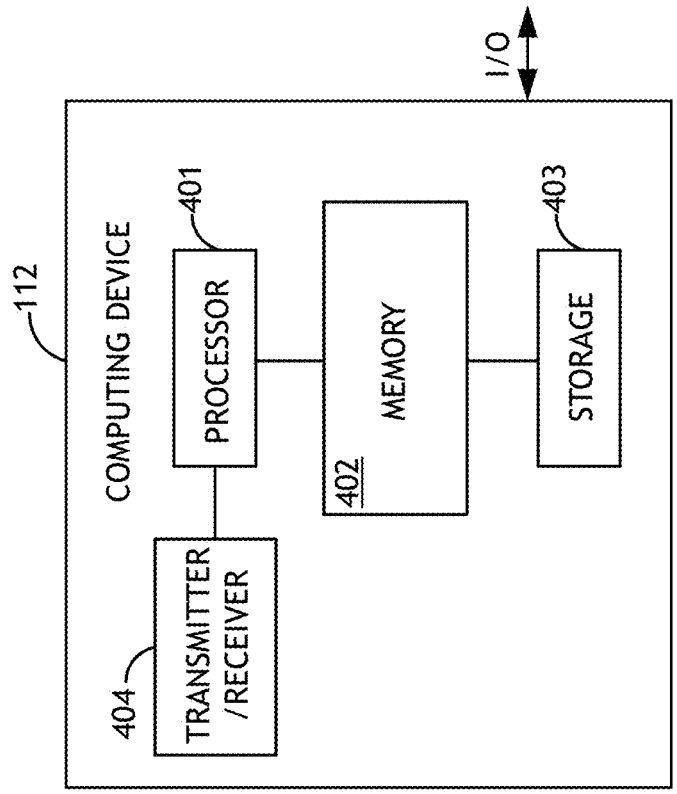
FIG. 4 depicts a computing device of an aircraft of one embodiment.

Referring now to FIG. 4, the computing device 112 (which may be referred to as the aircraft computing device) of the aircraft 110 of one embodiment is shown. The computing device 112 includes at least one processor 401, memory 402, storage 403, and a wireless communication component (e.g., a transmitter/receiver 404), as well as other components, equipment, and/or devices commonly included in a computing device. The processor 401, the memory 402, the storage 403, and the wireless communication component, as well as any other components may be communicatively coupled.

The wireless communication component may include or be implemented as a transmitter, receiver, and/or an antenna. The wireless communication component may be configured to wirelessly communicate (e.g., receive and/or send data or signals) with various devices of a vehicle (e.g., the aircraft 110) and/or elements of a system (e.g., system 100). For example, the wireless communication component may be configured to pair with and communicate with a wearable device 116, which may be worn by a vehicle operator (e.g., a pilot). The wireless communication component may be configured to communicate with any suitable wireless technology or standard, such as via Bluetooth, Near Field Communication (NFC), a local area wireless computing network (e.g., Wi-Fi), cellular networks, a mobile telecommunications network (e.g., third generation (3G), fourth generation (4G), or the like). The processor 401 may be configured to execute various software applications, instructions, or computer code stored in a non-transitory computer-readable medium (e.g., the memory 402 or the storage 403) causing the processor 401 to perform various operations, such as disclosed throughout. For example, the processor 401 may be configured to perform any of various operations on data received from the wearable device 116 or based on data received from the wearable device 116. For example, the processor 401 may be configured to monitor physiological data (e.g., oxygen level data, heart rate data, or the like) associated with a pilot. The processor 401 may determine if the pilot is experiencing any health problems (e.g., hypoxia, abnormal (e.g., low or high) heart rate, or the like) based on the physiological data. In response to a determination that the pilot is experiencing a health problem, the processor 401 may perform any of various operations. For example, in response to a determination that the pilot is experiencing a health problem the processor 401 may output health alert data which may cause an alert to be issued (e.g., as an aural alert such as via a speaker, a visual alert such as via a display or a light emitting diode (LED), a vibratory alert such as via a vibration unit, or the like), for example, to notify the pilot to take corrective action (e.g., to wear an oxygen mask if the pilot is experiencing hypoxia). Additionally, in response to a determination that the pilot is experiencing a health problem the processor 401 may send data (e.g., pilot health alert data and/or physiological data) to an onboard destination (e.g., onboard data recording system 119, other systems 117, display 114, a wearable device associated with another user, and/or the like) and/or an off-board destination (such as another vehicle (e.g., other aircraft 120), ground control station 130, and/or the like). Further, the processor 401 may be configured to send (e.g., continuously, periodically at predetermined intervals, periodically upon an occurrence of a detected event or data condition, or the like) physiological data and/or pilot health alert data to an onboard destination (e.g., onboard data recording system 119 to be recorded, other systems 117, display 114, a wearable device associated with another user, and/or the like) and/or an off-board destination. Further, the processor 401 may be configured to engage an auto-pilot system in response to detecting a health problem (e.g., hypoxia). Additionally, the processor 401 may be configured to alert another crew member in response to detecting a health problem (e.g., hypoxia) of a pilot.

Figure 5:
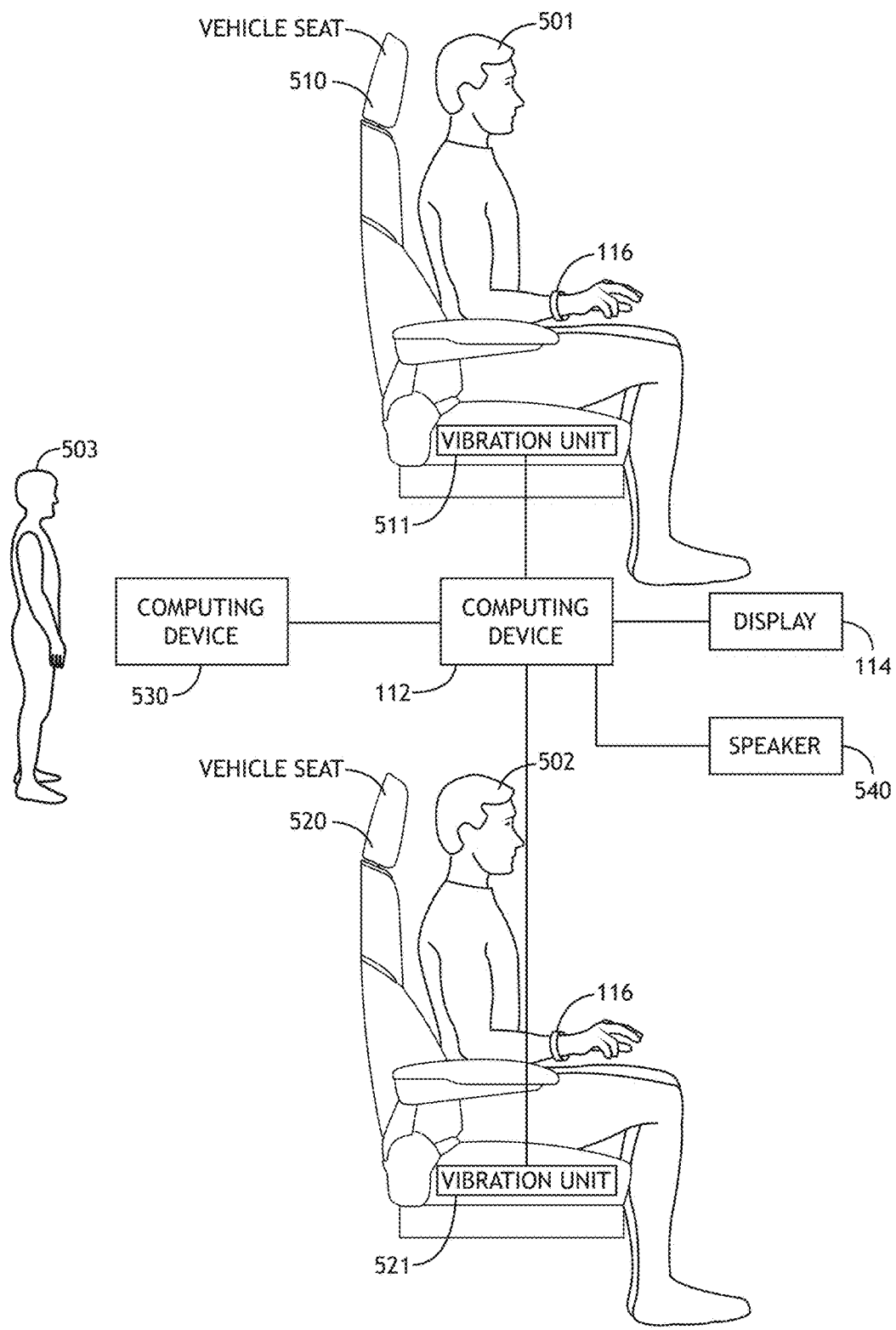
FIG. 5 depicts a diagram of some components of a vehicle of one embodiment.

Referring now to FIG. 5, a diagram of some components of a vehicle (such as the aircraft 110) is depicted. The vehicle may include computing device 112, computing device 530, display 114, speaker 540, vehicle seats 510, 520, and vibration units 511, 521. The vehicle may accommodate at least one person. For example, at least one person may include at least one operator (such as operator 501 and operator 502), at least one crew member (such as crew member 503), and/or at least one passenger. In some embodiments, operators 501, 502 may be pilots. As shown in FIG. 5, each of the operators 501, 502 are wearing wearable devices 116. The computing device 112, computing device 530, display 114, speaker 540, vehicle seats 510, 520, vibration units 511, 521, and wearable devices may be communicatively coupled.

The computing device 530 may be implemented as any of various suitable computing devices. The computing device 530 may include a processor, memory storage, an output component (e.g., a speaker, display, and/or a vibration unit), an input component (e.g., a keyboard, buttons, and/or touchpad), an input/output component (e.g., a touchscreen display), a communication component (e.g., wireless or non-wireless communication component), and/or any other components commonly included in computing devices. For example, the computing device 530 may be implemented as a mobile computing device (e.g., a tablet computing device, a smart phone, a laptop computing device, or the like). Additionally, for example, the computing device 530 may be implemented as a wearable device and include components as similarly described with respect to wearable device 116. Further, for example, the computing device 530 may be implemented within a portion of the vehicle (such as in the back of a seat).

The computing device 112 may be configured to perform any of various operations, such as disclosed throughout. For example, the computing device 112 may be configured to receive physiological data and/or pilot health alert data associated with the operators 501, 502, and/or other data from the wearable devices 116. If it is determined that one or more of the operators 501, 502 is experiencing a health problem (e.g., hypoxia), the computing device may cause an output device (e.g., display 114, speaker 540, vibration units 511, 521, and/or an output component of computing device 530) to issue an alert. For example, the display 114 may be configured to present a visual alert, the speaker 540 may be configured to output an aural alert, vibration units 511, 521 may be configured to generate a vibratory alert, and an output component (e.g., a speaker, display, vibration unit, or the like) of the computing device 530 may be configured to output a visual alert, an aural alert, or a vibratory alert.

As used throughout, "at least one" means one or a plurality of; for example, "at least one" may comprise one, two, three, . . . , one hundred, or more. Similarly, as used throughout, "one or more" means one or a plurality of; for example, "one or more" may comprise one, two, three, . . . , one hundred, or more.

In the present disclosure, the methods, operations, and/or functionality disclosed may be implemented as sets of instructions or software readable by a device. Further, it is understood that the specific order or hierarchy of steps in the methods, operations, and/or functionality disclosed are examples of exemplary approaches. Based upon design preferences, it is understood that the specific order or hierarchy of steps in the methods, operations, and/or functionality can be rearranged while remaining within the disclosed subject matter. The accompanying claims may present elements of the various steps in a sample order, and are not necessarily meant to be limited to the specific order or hierarchy presented.

It is believed that embodiments of the present disclosure and many of its attendant advantages will be understood by the foregoing description, and it will be apparent that various changes can be made in the form, construction, and arrangement of the components thereof without departing from the scope of the disclosure or without sacrificing all of its material advantages. The form herein before described being merely an explanatory embodiment thereof, it is the intention of the following claims to encompass and include such changes.

What is claimed is:

1. An aviation system, comprising:
   a wearable device configured to be worn by a pilot of an aircraft, including:
      at least one sensor configured to measure at least one physiological state of the pilot;
      at least one wearable device processor coupled to the at least one sensor; and
      a wearable device display coupled to the at least one wearable device processor;
      wherein the wearable device is configured to output at least one of physiological data indicative of the at least one physiological state of the pilot or pilot health alert data indicative of a determined health problem associated with the pilot; and
   at least one computing device implemented in the aircraft, including:
      at least one processor configured to:
         receive at least one of the physiological data associated with the pilot or the pilot health alert data from the wearable device;
         determine whether the pilot is experiencing a health problem based on at least one of the physiological data or the pilot health alert data;
         route at least a portion of at least one of the physiological data or the pilot health alert data to at least one control station;
         receive an instruction from the at least one control station to engage an autopilot system of the aircraft after routing at least the portion of at least one of the physiological data or the pilot health alert data to the at least one control station; and
         in response to receipt of the instruction from the at least one control station to engage the autopilot system of the aircraft, engage the autopilot system of the aircraft.

2. The aviation system of claim 1, wherein the at least one sensor includes an oximeter, and the physiological data includes oxygen level data.

3. The aviation system of claim 1, wherein the at least one wearable device processor is configured to determine whether the pilot is experiencing the health problem based on the physiological data.

4. The aviation system of claim 3, wherein the at least one sensor includes an oximeter configured to measure arterial oxygen saturation levels, the physiological data includes oxygen level data indicative of measured arterial oxygen saturation levels, and the at least one wearable device processor is configured to determine whether the pilot is experiencing hypoxia based on the oxygen level data.

5. The aviation system of claim 4, wherein the at least one sensor further includes a sensor configured to measure heart rate, the physiological data further includes heart rate data indicative of a measured heart rate, and the at least one wearable device processor is configured to determine whether the pilot is experiencing the health problem based at least on the heart rate data and the oxygen level data.

6. The aviation system of claim 3, wherein the at least one wearable device processor is configured to output the pilot health alert data to be routed to at least one output component onboard the aircraft to be issued as at least one of a visual alert, an aural alert, or a vibratory alert.

7. The aviation system of claim 3, wherein the at least one wearable device processor is configured to output the pilot health alert data to be routed to at least one output component onboard the aircraft to be issued as a vibratory alert configured to vibrate a seat of the pilot.

8. The aviation system of claim 3, wherein the wearable device is implemented as one of a wrist wearable device, a hand wearable device, a clothing wearable device, an adhesively-attached device, a helmet device, a goggle device, a visor device, or a glasses device.

9. The aviation system of claim 1, further comprising an onboard data recording system of the aircraft, wherein the onboard data recording system is configured to receive at least one of the pilot health alert data or at least some of the physiological data, and the onboard data recording system is configured to store at least one of received physiological data or received pilot health alert data.

10. The aviation system of claim 1, wherein the at least one processor of the at least one computing device is configured to receive updated flight plan data from the at least one control station after routing at least the portion of at least one of the physiological data or the pilot health alert data to at least one control station, and the at least one processor of the at least one computing device is configured to update a flight plan based on the updated flight plan data.

11. The aviation system of claim 1, wherein the at least one processor of the at least one computing device is configured to receive remote operation instructions from the at least one control station after routing at least the portion of at least one of the physiological data or the pilot health alert data to at least one control station, and the at least one processor of the at least one computing device is configured to operate the aircraft based at least on the remote operation instructions.

12. The aviation system of claim 1, wherein, in response to the determination that the pilot is experiencing the health problem, the at least one processor of the at least one computing device is configured to change a flight plan of the aircraft.

13. The aviation system of claim 1, wherein the wearable device is a wearable computing device.

14. The aviation system of claim 1, wherein the at least one wearable device processor is configured to output the pilot health alert data to an engine-indicating and crew-alerting system (EICAS).

15. A method, comprising:
receiving, by at least one processor of at least one computing device implemented in an aircraft and from a wearable device worn by a pilot of the aircraft, physiological data indicative of at least one physiological state of the pilot, wherein the wearable device includes at least one sensor including an oximeter, the physiological data includes oxygen level data, wherein the wearable device further includes at least one at least one wearable device processor coupled to the at least one sensor and a wearable device display coupled to the at least one wearable device processor;
determining, by the at least one processor of the at least one computing device, that the pilot is experiencing hypoxia based at least on the physiological data;
outputting, by the at least one processor of the at least one computing device, pilot health alert data upon a determination that the pilot is experiencing hypoxia;
routing, by the at least one processor of the at least one computing device, at least a portion of the pilot health alert data to at least one control station;
receiving, by the at least one processor of the at least one computing device, an instruction from the at least one control station to engage an autopilot system of the aircraft after routing at least the portion of the pilot health alert data to the at least one control station; and
in response to receipt of the instruction from the at least one control station to engage the autopilot system of the aircraft, engaging the autopilot system of the aircraft.

16. The method of claim 15, wherein outputting, by the at least one processor of the at least one computing device, pilot health alert data upon a determination that the pilot is experiencing hypoxia further comprises:

outputting, by the at least one processor of the at least one computing device, pilot health alert data to be routed to at least one output component onboard the aircraft to be issued as at least one of a visual alert, an aural alert, or a vibratory alert upon a determination that the pilot is experiencing hypoxia.

17. The method of claim 15, further comprising:
receiving, from the at least one control station, at least one of updated flight plan data or remote operation instructions after routing at least the portion of the pilot health alert data to the at least one control station.

18. The method of claim 15, further comprising:
changing a flight plan of the aircraft in response to the determination that the pilot is experiencing hypoxia.

19. A vehicular system, comprising:
a wearable device configured to be worn by an operator of a vehicle, including:
at least one sensor configured to measure at least one physiological state of the operator;
at least one wearable device processor coupled to the at least one sensor; and
a wearable device display coupled to the at least one wearable device processor;
wherein the wearable device is configured to output at least one of physiological data indicative of the at least one physiological state of the operator or operator health alert data indicative of a determined health problem associated with the operator; and
at least one computing device implemented in the vehicle, including:
at least one processor configured to:
receive at least one of the physiological data associated with the operator or the operator health alert data from the wearable device;
determine whether the operator is experiencing a health problem based on at least one of the physiological data or the operator health alert data;
route at least a portion of at least one of the physiological data or the operator health alert data to at least one control station;
receive an instruction from the at least one control station to engage an autopilot system of the vehicle after routing at least the portion of at least one of the physiological data or the operator health alert data to the at least one control station; and
in response to receipt of the instruction from the at least one control station to engage the autopilot system of the vehicle, engage the autopilot system of the vehicle.

* * * * *